United States Patent [19]

Glass et al.

[11] 4,259,445
[45] Mar. 31, 1981

[54] IMMOBILIZED ENZYME CATALYST

[75] Inventors: Richard W. Glass, Bryan, Tex.; Joseph Glogowski, Pawtuckett, R.I.

[73] Assignee: CPC International, Englewood Cliffs, N.J.

[21] Appl. No.: 44,729

[22] Filed: Jun. 1, 1979

[51] Int. Cl.³ .................... C12M 11/10; C12M 11/04; B01J 31/02
[52] U.S. Cl. ..................................... 435/178; 252/316; 252/426; 252/428; 252/429 R; 426/52; 435/182
[58] Field of Search .................. 252/426, 428, 429 R, 252/430, 316; 435/174–183; 426/50, 52

[56] References Cited

U.S. PATENT DOCUMENTS

| | | | |
|---|---|---|---|
| 3,063,912 | 11/1962 | Otaka et al. | 435/183 |
| 3,691,090 | 9/1972 | Kitajima | 435/182 |
| 4,102,745 | 7/1978 | Thompson et al. | 435/175 |

*Primary Examiner*—P. E. Konopka

[57] ABSTRACT

An enzyme catalyst is described. The catalyst comprises subcellular particulates of vegetable material containing an enzyme system composed of different carbohydrate transforming enzymes. These particulates are encapsulated within a matrix formed by coagulating an organic entrapping agent with polyvalent cations. The matrix is permeable to permit access of carbohydrate substrate to enzyme and acts to immobilize the enzyme system and preserve the activity of the encapsulated enzymes.

18 Claims, No Drawings

IMMOBILIZED ENZYME CATALYST

BACKGROUND OF THE INVENTION

There has been substantial research and commercial interest in enzyme immobilization technology. It has primarily focused upon simple, single enzyme systems; for example, ones which catalyze one-step degenerative or isomerization reactions. Immobilization has been accomplished by a number of means within the general categories of attachment of the enzyme to solid supports; entrapment within a porous gel; and various chemical linking techniques.

There has also been some interest in multi-enzyme systems. Commonly, this has involved immobilization of whole cell preparations. Immobilized cellular preparations have the additional advantage that they may contain co-factors native to the cells. These may accelerate desired single or multi-step reactions. Because whole cells are involved, however, use of these catalysts may be limited by complications arising from the native limits imposed by the cells themselves and by natural cellular metabolisms.

The use of immobilizing supports appears to have been practiced primarily to facilitate handling of enzymes during use. It is well known, for example, that immobilization permits treatment of greater amounts of substrate. It fixes the location of the enzyme within the reaction zone and readily allows separation of the treated substrate and/or product from enzyme after the reaction has occurred.

The fields of use of enzyme and immobilized enzyme systems in the prior art has been quite broad. For example, the isomerization of glucose with an enzyme present in immobilized, whole cell preparations is disclosed in *Biotechnol. Bioeng.*, 15, 565 by Vieth et al. (1973). Other representative mention of such systems and specific facets thereof may be found in *Immobilized Enzymes Preparation and Engineering Techniques*, Gutcho, Noyes Data Corporation (1974) and *Biotechnology and Bioengineering*, Vol. XIX, pp. 387-397 by Kierstan et al. (1977).

While immobilized enzyme catalysts for carbohydrate (especially sugar and starch conversion) reactions have particularly high commerical interests, a variety of complications have heretofore limited their use. Whole cell catalysts, for example, often lead to low yield and interfering by-products. Conversely, the number of enzyme steps necessary for a given conversion may make their use uneconomic.

In addition, any use of enzymes as catalysts requires consideration of their operational life, and this is no less the case in carbohydrate conversion reactions. A serious problem encountered in the use of enzymes (in immobilized or free form) involves their inactivation by constituents native to the enzyme source or produced during their isolation and/or use. Thus, there are numerous reports respecting inactivating agents and means for overcoming their effects. These include Baijal et al., *Phytochem.* 11:929 (1972); Hawker, *Phytochem.* 8:9 (1969); Palmer et al., *Aust. J. Biol. Sci.* 22:87 (1969); Burg et al., *Plant Physiol.* 39:185 (1964); and Sacher, *Nature* 195:577 (1962)—describing the adverse effects of phenolic content of many vegetable materials on enzyme activity—and Loomis et al., *Phytochem.* 5:423 (1966); Anderson, *Phytochem.* 7:1973 (1968); and Loomis, *Methods in Enzymol.* 31:258 (1974)—describing means for reducing enzyme inactivation resultant from the different browning reactions in vegetable materials.

In all fields of use, however, substantial impediments remain. Moreover, commercialization of enzyme catalysts in many has heretofore been wholly uneconomic because of these drawbacks.

SUMMARY OF THE INVENTION

In accordance with the present invention, a catalyst containing immobilized, subcellular particulates of vegetable material is employed. This vegetable material contains an enzyme system composed of different carbohydrate transforming enzymes and is immobilized within a permeable matrix comprising an organic entrapping agent coagulated with polyvalent cations.

Depending upon the conditions of use, the catalyst will aid in effecting a number of reactions. The specific enzymes present ordinarily include ones which catalyze hydrolysis-degenerative reactions, such as amylases of maltases or invertases; construction reactions, for instance those producing sucrose and even starches from mono-, di- or oligosaccharides; and/or isomerization reactions.

The present catalysts and the approach to their production differ substantially from those of the prior art. As a result, they are readily produced and generally evidence activities and utilities far exceeding those previously known. Instead of relying upon whole cell or individual enzyme preparations, the present invention is predicated upon immobilization of subcellular, vegetable material particulates. These particulates are intermediate in size and characteristics between individual enzymes and whole cell preparations. They contain enzyme systems composed of different carbohydrate transforming enzymes which have been found to possess certain characteristics quite distinct from prior art enzyme systems. In part, these characteristics are believed resultant from the enzymes' retention of their native cellular orientations (or proximate configurations) in the particulates.

To form the present catalysts, subcellular particulates are prepared by macerating an enzyme-containing vegetable material. These particulates are then combined with an organic entrapping agent which is coagulated (to encapsulate the particulates) with a polyvalent cation in conventional manner. Coagulation converts the organic agent into a carbohydrate-permeable matrix which provides the catalysts with unexpected properties. Most importantly, the matrices show an ability to preserve the activities of the immobilized (or entrapped) enzymes from inactivation. This greatly increases and lengthens their active life.

The present catalysts, and particularly their preservative matrices containing a multiplicity of enzymes, offer substantial advances over the prior art. Surprisingly, no inhibitory effects of high concentrations of any one of the products of the enzyme reactions have been found. Further, the net effect of the enzymes often appears to be more than that which might customarily be attributable to the enzymes individually.

DETAILED DESCRIPTION OF THE INVENTION

A virtually limitless spectrum of vegetable materials is available for use in forming the catalysts of the present invention. However, materials exhibiting high concentrations of carbohydrate transforming enzymes are preferred since these result in catalysts having correspondingly elevated carbohydrate conversion activities. Fruits which ripen quickly, for example, bananas, are particularly high in enzyme content. There are, therefore, particularly desirable.

This invention also appears to be particularly effective in alleviating the enzyme inhibitory effect of phenol. Consequently, it is especially useful in conjunction with vegetable materials, again including bananas, which natively exhibit a high (usually in excess of 200 mg/100 gm total weight) phenolic content.

Formation of the present particulates from the vegetable material may be performed by conventional means. Generally, the vegetable material is macerated by, for example, mechanical comminution. For this purpose, blenders and other such shear devices are most conveniently employed. In forming the particulates, maceration should be continued until particulates having subcellular size are obtained.

By this, it is not meant to be indicated that essentially all the particulates must be subcellular, although this is preferred. It is sufficient if the vegetable material be macerated to an extent such as the resultant particulates include a substantial proportion of fragmentary or partial cells. Preferably they contain at least 20%, most preferably at least 50%, cell fragments by total weight. This ensures that the ultimate catalysts will function on the basis of freely accessible individual enzyme systems, as opposed to native cells.

Once fragmented to subcellular particulates, the vegetable materials of the present invention become susceptible to a number of inhibitory effects. Much of this inhibition is due to the release of intracellular material and/or its subsequent reaction to produce inhibiting agents which may then interfere with the activity of the present enzyme systems. This inhibition is readily apparent and leads, in the absence of contravening measure, to complete enzymatic inactivation.

Of particular significance in this respect are inhibitors commonly believed resultant from "browning reactions". Browning reactions, both enzymatic and non-enzymatic, are recognized to be associated with many vegetable materials. For example, they include such reactions as the polymerization and oxidation of phenolic compounds and the Maillard reactions. Many of these reactions are known to proceed via highly reactive intermediates which may be responsible for the inactivation of many enzymes. There are also native cellular constituents which appear, upon release from a cell, to be detrimental. Of these constituents, phenols (including polyphenols) are believed most important insofar as inactivation of enzymes is concerned. All these side effects of the particularization of cells represent major drawbacks which have limited the use of subcellular particulates or particles in enzyme catalysts.

In accordance with the present invention, the foregoing and similar inhibitory effects are at least strongly suppressed. Although the mechanism for this result remains uncertain, it has been discovered that the instant use of matrices composed of cationically gelled entrapping agents somehow acts to protect the enzymes from normal inactivation.

The entrapping agents employed to form these preservation matrices are individually well known. They include such organic compounds as methoxy pectin and alginates. Similarly, it is well known that they can be gelled with a polyvalent cation such as aluminum, more preferably a divalent cation such as zinc, copper and, especially, calcium.

Encapsulation of the subcellular particulates of vegetable material within these matrices is readily accomplished. Most conveniently, the desired amount of particulates, for example, between about 10 and 35% by total weight, is suspended within an aqueous solution containing between about 0.5 and 3.0%, most preferably 1 to 2%, by weight of the entrapping agent. This suspension may then be contacted with an aqueous solution containing the polyvalent cation in, for example, a concentration of from 3 to 15% of cation weight. Contact may be accomplished in a number of ways, most conveniently simply by dripping the suspension slowly into the cationic solution. The matrix is formed almost instantaneously.

In the foregoing case of dropwise addition, the matrix (and consequently, the catalyst) formed assumes a bead-like configuration. Such beads are particularly useful because they may be employed to pack columns for continuous processing or be added to chambers for batch processing. Any other catalyst configurations are within the scope of this invention. Depending upon the manner of formation, plates and similarly diverse physical forms of entrapped catalyst may be produced.

In forming the matrices, it is important to ensure that they remain carbohydrate-permeable. This permits ready access of substrate to the immobilized enzymes. This may be accomplished by means known in the art, for example, simply by utilizing the appropriate concentrations of the entrapping agent such as those set forth hereinabove. Desired degrees of permeability will, however, obviously depend upon the effective molecular sizes of the substrates and products with which a given catalyst is intended to be used.

In general, it is preferred to limit the size of the catalysts to ensure optimum access of substrate to enzyme. This is readily accomplished through control of the coagulating step, and catalysts having at least one dimension (or thickness) of betwen about 0.5 to 10mm, preferably 1 to 5mm are most desirable.

Encapsulation of subcellular particulates within the present matrices does not always obviate browning reactions. Nonetheless, it substantially preserves the activities of the encapsulated enzymes. Apparently, this is accomplished at least partially through interference with the production of various of the by-products of browning reactions which would interfere with or inactivate the enzymes.

To ensure preservation of enzyme activity, the matrix can be subjected to leaching or washing. This step removes intermediates and products formed incident to the browning reaction of the encapsulated vegetable material particulates which could inhibit enzyme activity. The leaching or washing may be accomplished in conventional manner, generally utilizing an aqueous solution which may be buffered to retain optimum enzyme activity. Alternatively, instead of being performed as a separate step, the separation of inactive and possibly detrimental products may be accomplished by placing the catalysts in a deep bed reactor such as filter plates and columns, and washing with a solution containing stabilizing agents, for example, ions and/or substrates such as carbohydrates.

A still further means of ensuring enzyme activity lies in the use of conventional anti-browning agent which may be incorporated within the matrix. These anti-browning agents, such as cysteine-HCl or polyvinyl pyrolidone (PVP) may, for example, be incorporated within the catalyst by inclusion in the suspension of vegetable material and entrapping agents, the cationic solution and/or adding during the separation of inactive products.

Inside a matrix, specific enzymes among the different ones present assume major importance depending upon the desired use of the catalyst and the selected operating conditions. Among the most important of these enzymes are the following:

Alpha-amylase—this enzyme generally cleaves starch essentially randomly;

Beta-amylase—this enzyme generally cleaves maltose groups from the ends of starch and starch fragments;

Maltase—this enzyme cleaves the disaccharide maltose into its constituent glucose moieties;

Invertase—this enzyme cleaves the disaccharide sucrose into its constituents, fructose and glucose.

Many other enzymes may also be present in a matrix. They include, for example, sucrose synthetase which catalyzes the reactions:

UDP-glucose+fructose⇌sucrose+UDP and

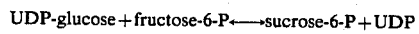

UDP-glucose+fructose-6-P⇌sucrose-6-P+UDP and the like. They may, in the manner discussed hereinbelow, become significant through cooperation with one or more of the preceding major enzymes.

In addition to the enzymes immobilized in the matrices of the catalysts, other catalytic components may be present with attendant increases in catalytic efficiency. The most important of these other components are the enzymatic co-factors often involved in carbohydrate reactions. These co-factors, such as UDP, UDP-glucose, phosphate and fructose-6-phosphate, are to some extent mobile within the matrix for cooperation in the catalytic reactions. This limited freedom and consequent contribution to catalytic activity may substantially improve the overall yield and efficiency exhibited during use of the present catalysts in any given carbohydrate synthesis or degradation process. These co-factors may be present within the matrices either by virtue of having been encapsulated with the enzymes or through addition to substrate feed during use of the catalyst.

Actual use of the present catalysts may be made in conventional manner. Ordinarily the catalyst beads are packed into a column or bed. Carbohydrate substrate, generally in dilute aqueous solution, is then passed through the bed at a rate which permits optimum yield of the desired product.

The particular carbohydrate substrate or starting material feed solution for the enzymatic conversion is obviously dependent upon the desired reaction. Its selection, is, however, evident from the preceding discussion of enzymes and from the prior art.

As will become apparent from the Examples which follow and from prior discussion, the feed solution may additionally contain ingredients which will increase the yield and/or efficiency of the desired conversion. The presence of these accelerator and/or stabilizing ingredients is a preferred aspect of the present invention.

In employing the present catalysts in a sugar or starch process, it is desirable to control at least certain process conditions in order to optimize production of the desired end product. Otherwise, the plurality of active enzymes present in the catalyst might lead to production of a product quite distinct from that intended or to an unusable product mixture. This may be accomplished in conventional manner. It has been recognized that various conditions, most particularly pH and substrate composition, will permit the suppression of various undesired reactions and the accentuation of the activity of a desired enzyme to increase yield of desired product.

Representative examples of the present catalysts and their uses in specific processes are described in the following examples. It is emphasized, however, that these examples are intended to be only illustrative of the present invention and that its scope is not limited thereby.

EXAMPLE I

The invertase activities of beads formed from different entrapping agents (with and without additive anti-browning agents) were examined to obtain an index of enzyme activity within the catalysts. The tested catalysts were formed by encapsulation of subcellular particulates of vegetable material and 1% aqueous solutions of two different forms of alginate (Kelco and Protanal) and 1% and 2% by weight low methoxy pectin solutions. In parts of the tests, coagulation was performed utilizing calcium chloride solutions containing 1% PVP and .025% cystine-hydrochloride as anti-browning agents.

To produce the catalysts, 75 grams of the pulp of ripe, yellow, #7 bananas were cut into slices approximately 5 mm thick and dispersed in 250 ml of aqueous solution of the entrapping agent. To ensure retention of activity, the solutions contained a buffer to maintain a neutral biological pH of about 7.5. The solutions containing the sliced pulp were stored with gentle shaking overnight at 37° C. and then homogenized in a blender for 1 minute.

The homogenate was then decanted into a wide-tipped buret and allowed to drop slowly into a 10% calcium chloride solution, also buffered to a pH of 7.5. As drops of the homogenate fell into the stirred calcium chloride solution, beads entrapping or encapsulating the homogenate were rapidly formed and removed with a strainer.

For the tests, sample beads were dialyzed for 48 hours at 4° C. Dialysis removed the sugar content of the matrix-encapsulated vegetable material. This permitted monitoring of the enzyme activity through use of a YSI model 23A Glucose Analyzer (Yellow Springs Instrument Company) by providing a base line constant which would reflect changes in glucose concentration due to the catalyst. The beads were then placed in a column which was then filled with buffered water to provide a base line for glucose concentration.

The results for the base line constants were as follows, glucose activity being given in milligrams per deciliter (mg/dl):

TABLE 1

| Invertase Activity of Beads (with anti-browning agents) | |
|---|---|
| No Substrate | Glucose (mg/dl) |
| Kelco Beads | 5 |
| Protanal Beads | 5 |
| 1% Pectin Beads | 8 |
| 2% Pectin Beads | 3 |

| Invertase Activity of Beads (without anti-browning agents) | |
|---|---|
| No Substrate | Glucose (mg/dl) |
| Kelco Beads | 3 |
| Protanal Beads | 2 |
| 1% Pectin Beads | 1 |

TABLE 1-continued

| 2% Pectin Beads | 2 |
|---|---|

The activity of beads was then analyzed over appropriate periods of time with a carbohydrate substrate or feed of a 1% sucrose solution buffered as set forth above. The data set forth in Table 2 reflect averages of two separate trials for each of the bead-types.

TABLE 2

Invertase Activity of Beads (with anti-browning agents)

| With Sucrose Substrate | Glucose (mg/dl) | |
|---|---|---|
| | 1 hour | 2 hours |
| Kelco Beads | 20 | 46 |
| Protanal Beads | 11 | 24 |
| 1% Pectin Beads | 14 | 32 |
| 2% Pectin Beads | 10 | 24 |

Invertase Activity of Beads (without anti-browning agents)

| With Sucrose Substrate | Glucose (mg/dl) | |
|---|---|---|
| | 1 hour | 2 hours |
| Kelco Beads | 14 | 30 |
| Protanal Beads | 12 | 25 |
| 1% Pectin Beads | 14 | 32 |
| 2% Pectin Beads | 11 | 25 |

All matrices clearly serve to preserve the activities of the encapsulated enzymes from inactivation. The degree of effectiveness of the catalysts is also somewhat dependent upon the particular entrapping agent utilized in forming the protective matrix. Comparison of similar beads in Table I (no added substrate for reaction) and Table 2 (sucrose substrate) shows significant activities are involved.

Comparison of similar beads, with and without additional anti-browning agents from the paired halves of Table 2, shows that in some instances such additives appear unnecessary. While Kelco Beads reflect the further preservative advantage of anti-browning agents, the other bead-types are at least as active without the anti-browning agent additives as where such are present.

EXAMPLE II

To investigate the activities of various further enzymes, catalysts were prepared from Kelco alginate entrapping agent in the manner set forth in Example I and were analyzed on various substrates for production of glucose as set forth there. The results of these different tests are recorded below in Table 3. The substrates identified (soluble starch and/or maltose) were varied dependent upon the activity of the enzyme being examined.

TABLE 3

| | pH | Initial | Glucose (mg/dl) After 1½ hrs. | After 8 hrs | After 23 hrs. |
|---|---|---|---|---|---|
| Amylase | | | | | |
| Beads | 6.0 | 0 | 1 | 1 | 1 |
| Starch (1%) | 6.0 | 1 | 1 | 1 | 2 |
| Beads & Starch (1%) | 6.0 | 9 | 3 | 12 | 21 |
| Amylase | | | | | |
| Beads | 4.8 | 0 | 1 | 1 | 1 |
| Starch (1%) | 4.8 | 0 | 0 | 1 | 1 |
| Beads & Starch (1%) | 4.8 | 0 | 1 | 4 | 5 |
| Invertase | | | | | |
| Beads | 4.8 | 1 | 1 | 1 | 1 |
| Sucrose (1%) | 4.8 | 0 | 2 | 1 | 0 |
| Beads & Sucrose (1%) | 4.8 | 0 | 48 | 250 | 497 |

TABLE 3-continued

| | pH | Initial | Glucose (mg/dl) After 1½ hrs. | After 8 hrs | After 23 hrs. |
|---|---|---|---|---|---|
| Maltase | | | | | |
| Maltose (0.1%) | 6.0 | 0 | 2 | — | — |
| Beads | 6.0 | 1 | 0 | — | — |
| Maltose (0.1%) & Beads | 6.0 | 0 | 28 | — | — |
| Starch (1%) | 6.0 | 2 | 1 | — | — |
| Starch (1%) & Beads | 6.0 | 1 | 5 | — | — |
| Starch (1%) & Maltose (0.1%) | 6.0 | 0 | 1 | — | — |
| Starch (1%), Maltose (0.1%) & Beads | 6.0 | 0 | 31 | — | — |

The data show that the activities of various of the different enzymes within the catalysts may be accentuated through selection of the optimum pH therefor during enzymatic processing. Even though glucose production is only a secondary measure of amylase activity (because glucose is only incidentally a product of amylase activity), the tests reflect in each instance the activity of the enzymes in the present catalysts for the desired enzymatic processes.

EXAMPLE III

Kelco alginate bead catalysts were prepared in accordance with the procedure set forth in Example I. The invertase activity of these beads was then monitored to determine the effects of addition of the co-factors, UDP-glucose and/or fructose-6-phosphate, in 1% sucrose solutions. The result of these tests are set forth below in Table 4.

TABLE 4

| Reagents | Initial | After 12 hrs. | After 24 hrs. | After 48 hrs. | After 72 hrs. |
|---|---|---|---|---|---|
| 1. 1% Sucrose | 2 | 28 | 253 | 349 | 337 |
| 2. UDP-Glucose | 1 | 1 | 0 | 0 | 1 |
| 3. F-6-P | 1 | 1 | 2 | 2 | 2 |
| 4. UDP-Glucose & F-6-P | 2 | 2 | 1 | 1 | 2 |
| 5. 1% Sucrose & UDP-Glucose | 1 | 88 | 661 | 1227 | 1301 |
| 6. 1% Sucrose & F-6-P | 2 | 22 | 33 | 23 | 12 |
| 7. 1% Sucrose & UDP-Glucose F-6-P | 2 | 13 | 14 | 12 | 12 |

The foregoing data reflect that invertase activity may be reduced by the addition of fructose-6-phosphate alone or fructose-6-phosphate and UDP-glucose. In the presence of UDP-glucose alone, however, invertase activity is dramatically and unexpectedly increased. Because the 1% level of sucrose present in the starting material is capable of producing only 1,000 mg/dl (and 1301 mg/dl was actually produced in run 5), a new mechanism of activity requiring the cooperative interaction of at least two enzymes is suggested. The achieved amount of glucose produced in run 5 means that, unlike the case where UDP-glucose alone was present (see run 2), this co-factor was involved in glucose production.

Not only do the data show a tremendous increase in rate of glucose production, but they also strongly infer the existence of a cyclic pathway in the catalysis of run 5 which involves both the biosynthesis and hydrolysis of sucrose. This speculated pathway can be illustrated as follows:

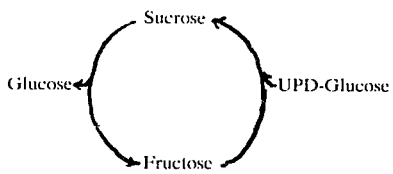

This proposed pathway explains the increased production of glucose. The mode of action would be that sucrose is hydrolyzed by invertase to yield fructose and glucose. Fructose is then condensed with available UDP-glucose to produce sucrose; and this newly synthesized sucrose is itself hydrolyzed to yield additional free glucose, beyond the 1,000 mg/dl theoretical maximum for the original 1% sucrose present.

Such cooperation between multiple enzymes appears in large part to be possible only because the enzymes of the system substantially retain their orientations on the particulates within the matrices of the catalysts. Disruption of these orientations would probably largely limit the catalyst activities to the sum of the activities of isolated and independent enzymatic reactions.

EXAMPLE IV

The process of Example III was repeated utilizing a sucrose level of 0.1%. At this reduced level of sucrose concentration, however, the cooperative cyclic pathway evidenced by run 5 of Table 4 was not encountered. This shows that the UDP-glucose and sucrose combination pathway is activated only above a threshold sucrose concentration sufficient to effect increased production of glucose from UDP-glucose.

What is claimed is:

1. A catalyst comprising subcellular particulates of vegetable material containing an enzyme system composed of different carbohydrate-transforming enzymes and being immobilized within a solid, carbohydrate-permeable matrix wherein the matrix contains an anti-browning agent, said matrix functioning to inhibit inactivation of said enzymes.

2. The catalyst of claim 1, wherein the matrix comprises an organic entrapping agent coagulated with polyvalent cation.

3. The catalyst of claim 2, wherein the matrix additionally contains UDP—glucose.

4. The catalyst of claim 1 wherein the particulates are comprised of phenol-containing vegetable material.

5. The catalyst of claim 1, wherein the matrix additionally contains sucrose.

6. The catalyst of claim 1, wherein the enzymes of the system substantially retain their native cellular orientations within the particulates.

7. The catalyst of claim 5, wherein the enzyme system contains invertase.

8. The catalyst of claim 7, wherein the enzyme system contains amylase.

9. The catalyst of claim 7, wherein the matrix additionally contains UDP—glucose and an amount of sucrose effective to induce production of glucose therefrom.

10. The catalyst of claim 9, wherein the enzymes of the system substantially retain their native cellular orientations within the particulates.

11. The catalyst of claim 2, wherein the entrapping agent is selected from the group consisting of pectin and alginate.

12. The catalyst of claim 11, wherein the entrapping agent is coagulated with calcium ion.

13. The catalyst of claim 1, wherein the matrix has been washed to inhibit enzyme inactivation.

14. The catalyst of claim 2, wherein the matrix is coagulated in the form of beads or plates having a thickness of from about 0.5 to 10 mm.

15. A process for the production of a catalyst having subcellular particulates of vegetables material containing an enzyme system composed of different carbohydrate-transforming enzymes and being immobilized within a solid, carbohydrate-permeable matrix comprised of an organic entrapping agent coagulated with polyvalent cation, said matrix functioning to inhibit inactivation of said enzymes, comprising macerating enzyme-containing vegetable material to produce subcellular particulates, combining said particulates with an aqueous coagulating agent and with divalent cation to encapsulate said particulates in a preservative matrix followed by dialyzing the matrix.

16. A process for the production of a catalyst having subcellular particulates of vegetable material containing an enzyme system composed of different carbohydrate-transforming enzymes and being immobilized within a solid, carbohydrate-permeable matrix comprised of an organic entrapping agent coagulated with polyvalent cation, said matrix functioning to inhibit inactivation of said enzymes, comprising macerating enzyme-containing vegetable material wherein said vegetable material is macerated in the presence of an anti-browning agent, to produce subcellular particulates, and combining said particulates with an aqueous coagulating agent and with divalent cation to encapsulate said particulates in a preservative matrix.

17. The process of claims 15 or 16 wherein the coagulating agent is selected from the group consisting of pectin and alginate.

18. The process of claims 15 and 16 wherein the matrix is coagulated in the form of beads or plates having a thickness of from about 0.5 to 10 mm.

* * * * *